United States Patent
Nagasawa et al.

[11] Patent Number: 5,996,395
[45] Date of Patent: Dec. 7, 1999

[54] FRICTIONAL DYNAMIC CHARACTERISTIC MEASURING APPARATUS

[75] Inventors: Yuji Nagasawa; Masakatsu Kuroishi; Hitoshi Nagata; Kunihiko Ando; Noriyasu Yamada, all of Aichi-ken, Japan

[73] Assignee: Kabushiki Kaisha Toyota Chuo Kenkyusho, Aichi-ken, Japan

[21] Appl. No.: 08/984,949

[22] Filed: Dec. 4, 1997

[51] Int. Cl.⁶ .............................. G01N 19/02; G01N 3/56
[52] U.S. Cl. .............................................. 73/9; 73/7
[58] Field of Search .................................. 73/7, 9

[56] References Cited

U.S. PATENT DOCUMENTS

| | | | |
|---|---|---|---|
| 3,992,922 | 11/1976 | Noble | 73/9 |
| 4,594,878 | 6/1986 | Abe et al. | 73/9 |
| 5,315,860 | 5/1994 | Drellich et al. | 73/9 |
| 5,375,451 | 12/1994 | Sandstrom | 73/7 |
| 5,736,630 | 4/1998 | Welner et al. | 73/9 |

FOREIGN PATENT DOCUMENTS 5-126683  5/1993  Japan.

*Primary Examiner*—Max Noori
*Attorney, Agent, or Firm*—Oblon, Spivak, McClelland, Maier & Neustadt, P.C.

[57] ABSTRACT

A frictional dynamic characteristic measuring apparatus for measuring a pressing force and a frictional force acting between a friction material as a specimen and a slide portion which are in sliding contact, includes a sliding speed changing device for forcibly changing a sliding speed of the friction material and the slide portion, which is changing in a self-excited manner at a resonance frequency of a resonance system including the friction material and the slide portion, at the resonance frequency of the resonance system. This apparatus enables evaluation of a friction material which absorbs self-excited vibration in a torsional vibration system without the need of additional evaluation in an actual machine for use.

20 Claims, 6 Drawing Sheets

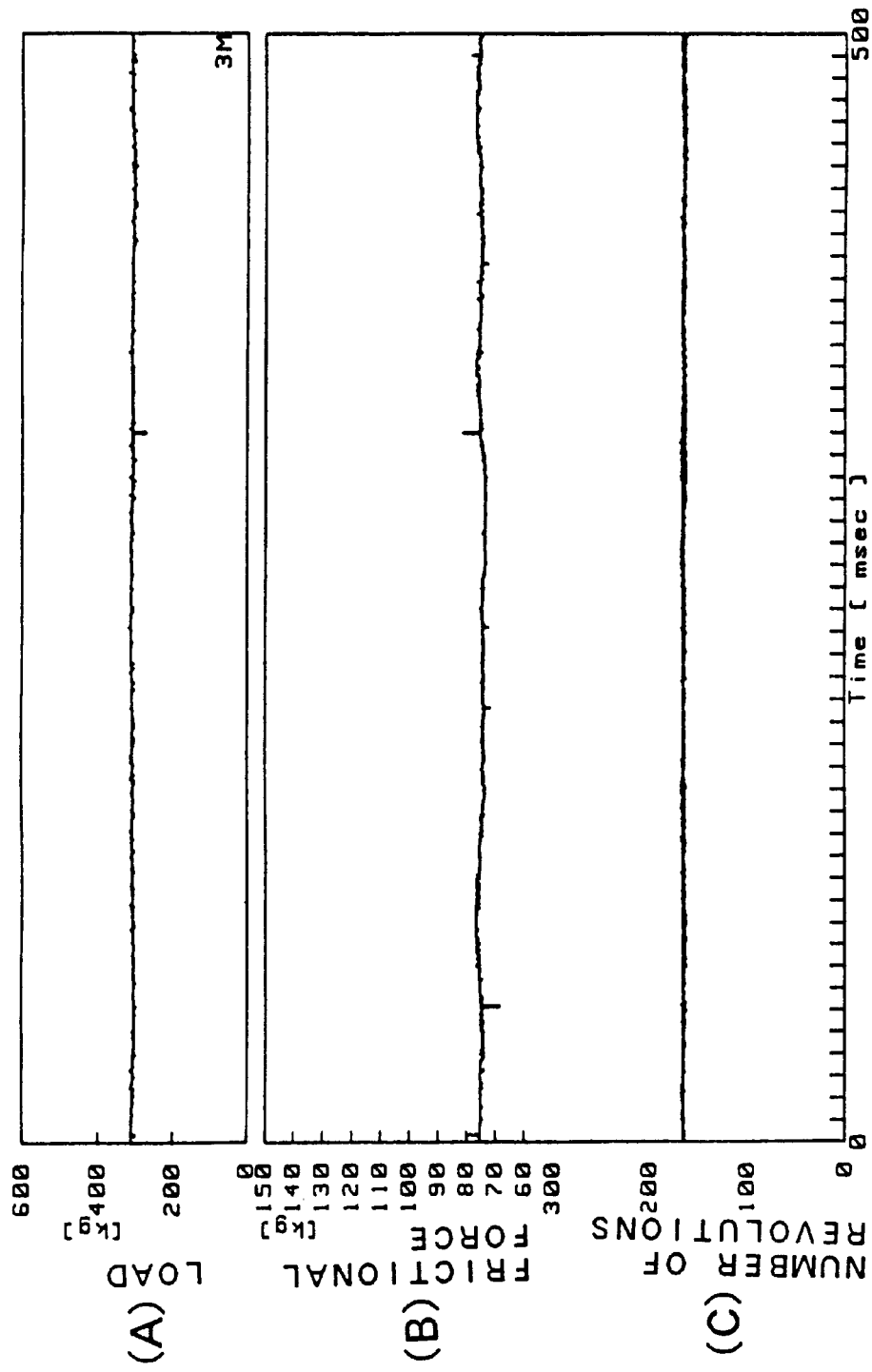

FRICTIONAL DYNAMIC CHARACTERISTIC MEASURING APPARATUS

BACKGROUND OF THE INVENTION

1. Field of the Invention

The present invention relates to a frictional dynamic characteristic measuring apparatus for measuring a pressing force and a frictional force acting between a friction material as a specimen and a slide portion when the friction material and the slide portion are in sliding contact. The frictional dynamic characteristic measuring apparatus of the present invention comprises a sliding speed changing means for self-excitedly changing a sliding speed of the friction material and the sliding portion at a resonance frequency of a resonance system including the friction material and the slide portion, and for forcibly changing the sliding speed of the friction material and the sliding portion at the resonance frequency of the resonance system, thereby enabling evaluation of the possibility of occurrence of vibration of the friction material that absorbs self-excited vibration of a torsional vibration system.

2. Description of the Related Art

Frictional vibration sometimes occurs in an apparatus for driving or braking using a friction material. If the velocity gradient of the friction coefficient of the friction material during the frictional vibration can be measured by a measuring apparatus under the same conditions as for actual frictional vibration in the aforementioned apparatus, it becomes possible to take countermeasures against frictional vibration in the aforementioned apparatus considering characteristics of only the friction material, thereby simplifying tests in the aforementioned apparatus or the like.

Since the aforementioned frictional vibration is greatly dependent on the velocity gradient of friction coefficient ($d\mu/dV$ value), the characteristic is used as an evaluation item. If the velocity gradient of friction coefficient is negative, frictional force, that is, the product of a load that perpendicularly acts on a friction surface of the friction material and a friction coefficient of a vibrating body on the friction surface, acts to maintain the vibration or to increase the vibration amplitude, corresponding to a speed change caused by vibration.

Conventionally, to measure the velocity gradient of a friction coefficient for evaluation of a friction material alone, a change in the friction coefficient relative to an objective velocity range or a specific velocity range is determined by selecting several velocities within such a range and measuring a friction coefficient at each velocity selected, i.e. at a constant velocity. However, this method does not determine an appropriate velocity gradient since the velocity changes in accordance with oscillation frequency under actual vibrating conditions. Therefore, the conventional method for measuring friction characteristic of a friction material alone cannot predict an actual phenomenon, but requires further evaluation in an actual use for final verification, in addition to the material evaluation, thus requiring considerable time and labor.

In conventional test apparatuses (Japanese Patent Laid-Open No. Sho 62-832, Japanese Patent Laid-Open No. Hei 05-126683) for simulating vibrations that occur in actual apparatuses, a vibration system similar to that in an actual apparatus is set up and realized in a test apparatus, and vibrations expected to occur in the actual apparatus are simulated. Depending on whether vibration occurs in the test apparatus, occurrence of vibrations in the actual apparatus is predicted.

The aforementioned conventional vibration simulating test apparatus simulates vibrations expected to occur in an actual apparatus, and makes it possible to predict occurrence of vibrations in the actual apparatus depending on whether vibration occurs in the test apparatus. There is a problem, however, that what can be evaluated by this apparatus is limited to materials capable of causing frictional vibrations equal to or greater than a certain extent.

More specifically, the conventional vibration simulating test apparatus has a problem that it merely evaluates whether the frictional material is a material that allows friction vibrations.

FIGS. 5 and 6 indicate results of measurement of materials with different evaluations as for frictional vibration. Material A in FIG. 5 is a material that readily undergoes frictional vibration, so that material A vibrates at an eigenfrequency of the friction characteristic measuring apparatus. On the other hand, material B in FIG. 6 is a material that does not readily undergo frictional vibration, that is, a material that has a characteristic of absorbing self-excited vibration in a torsional vibration system, so that no vibration occurs. This evaluation apparatus can evaluate materials in terms of whether vibration occurs, if the characteristics of materials considerably differ as in material A and material B. However, if a third material C undergoes no vibration as in material B, the superiority between material C and material B cannot be determined. Thus, this evaluation apparatus has a problem of incapability to evaluate the possibility of occurrence of vibration in a friction material having a characteristic of absorbing self-excited vibration in a torsional vibration system.

SUMMARY OF THE INVENTION

It is an object of the present invention to provide a frictional dynamic characteristic measuring apparatus that enables evaluation of possibility of occurrence of vibration in a friction material that absorbs self-excited vibration in a torsional vibration system, as well as evaluation of tendency of the friction material to vibrate.

It is another object of the present invention to provide a frictional dynamic characteristic measuring apparatus based on a technical idea for measuring a pressing force and a frictional force acting between a friction material as a specimen and a slide portion when the friction material and the slide portion are in sliding contact, wherein the sliding speed of the friction material and the slide portion is changed in a self-excited manner at a resonance frequency of a resonance system including the friction material and the slide portion, and the sliding speed of the friction material and the slide portion is forcibly changed at the resonance frequency of the resonance system.

It is a further object of the present invention to provide a frictional dynamic characteristic measuring apparatus for measuring a pressing force and a frictional force acting between a friction material and a slide portion which are in sliding contact, comprising a sliding speed changing member for forcibly changing, at a resonance frequency of a resonance system, a sliding speed of the friction material and the slide portion, which changes in a self-excited manner at the resonance frequency of the resonance system, the resonance system including the friction material and the slide portion.

It is a still further object of the present invention to provide a friction dynamic characteristic measuring apparatus comprising holding means for holding a friction material; slide portion slidingly contacting the friction material;

pressing means for pressing the slide portion to the friction material; sliding means for sliding the slide portion and the friction material; pressing force detecting means for detecting a pressing force of the pressing means; frictional force detecting means for detecting a frictional force that occurs between the slide portion and the friction material; first sliding speed changing means for self-excitedly changing a sliding speed of the friction material and the sliding means at a resonance frequency of a resonance system comprising the friction material, the holding means and the slide portion; and second sliding speed changing means for forcibly changing the sliding speed of the friction material and the sliding means at the resonance frequency of the resonance system.

It is a yet further object of the present invention to provide a frictional dynamic characteristic measuring apparatus wherein the second sliding speed changing means comprises external force changing means for changing an external force acting on the resonance system.

It is a yet further object of the present invention to provide a frictional dynamic characteristic measuring apparatus wherein the external force changing means comprises pressing force changing means for changing a pressing force.

It is another object of the present invention to provide a frictional dynamic characteristic measuring apparatus wherein the external force changing means comprises braking force applying means for applying a braking force to a rotating body in the resonance system.

A frictional dynamic characteristic measuring apparatus according to a first aspect of the present invention is a frictional dynamic characteristic measuring apparatus for measuring a pressing force and a frictional force acting between a friction material as a specimen and a slide portion when the friction material and the slide portion are in sliding contact, wherein the apparatus forcibly changes, at a resonance frequency of the resonance system a sliding speed of the friction material and the slide portion, which changes in a self-excited manner at the resonance frequency of a resonance system including the friction material and the slide portion.

A frictional dynamic characteristic measuring apparatus according to a second aspect of the present invention is an apparatus wherein a slide portion for slidingly contacting a friction material that is, the specimen held by the holding means is pressed against the friction material by the pressing means, and the sliding means slides the slide portion and the friction material, and the first sliding speed changing means changes a sliding speed of the friction material and the sliding means in a self-excited manner at a resonance frequency of a resonance system comprising the friction material, the specimen holding means and the slide portion, and the second sliding speed changing means forcibly changes the sliding speed of the friction material and the sliding means at a resonance frequency of the resonance system, and in this state, the pressing force detecting means detects a pressing force and the frictional force detecting means detects a frictional force that occurs between the slide portion and the friction material.

According to a third aspect of the present invention, the frictional dynamic characteristic measuring apparatus of the present invention is an apparatus wherein the external force changing means constituting the second sliding speed changing means changes an external force that acts on the resonance system.

According to a fourth aspect of the present invention, the frictional dynamic characteristic measuring apparatus of the present invention is an apparatus wherein the pressing force changing means constituting the external force changing means changes a pressing force.

According to a fifth aspect of the present invention, the frictional dynamic characteristic measuring apparatus of the present invention is an apparatus wherein the braking force applying means constituting the external force changing means applies a braking force to a rotating body in the resonance system.

The frictional dynamic characteristic measuring apparatus of the first aspect of the present invention achieves an advantages of enabling prediction of possibility of occurrence of vibration in a friction material that absorbs self-excited vibration in a torsional vibration system, since the sliding speed changing means forcibly changes a sliding speed of the friction material and the slide portion, which is changing in a self-excited manner at a resonance frequency of a resonance system including the friction material and the slide portion, at the resonance frequency of the resonance system.

The frictional dynamic characteristic measuring apparatus of the second aspect of the present invention achieves an advantage of enabling prediction of possibility of occurrence of vibration in a friction material that absorbs self-excited vibration in a torsional vibration system, since the pressing force detecting means detects a pressing force and the frictional force detecting means detects a frictional force that occurs between the slide portion and the friction material in a state where the first sliding speed changing means self-excitedly changes a sliding speed of the friction material and the sliding means at a resonance frequency of a resonance system comprising the friction material, the specimen holding means and the slide portion, and where the second sliding speed changing means forcibly changes the sliding speed of the friction material and the sliding means at the resonance frequency of the resonance system.

The frictional dynamic characteristic measuring apparatus of the third aspect of the present invention achieves an advantage of facilitating control of change in the sliding speed and evaluation of a friction material since the external force changing means changes an external force that acts on the resonance system.

Since the pressing force changing means changes pressing force, the frictional dynamic characteristic measuring apparatus of the fourth aspect of the present invention achieves an advantage of facilitating control of change in the sliding speed and evaluation of a friction material.

Since the braking force applying means applies a braking force to the rotating body in the resonance system, the data measured by the friction characteristic measuring portion is free from changes in load, eliminating the need to consider load gradient. Therefore, the frictional dynamic characteristic measuring apparatus of the fifth aspect of the present invention achieves an advantage of facilitating data arrangement.

BRIEF DESCRIPTION OF THE DRAWINGS

FIG. 6 shows graphs indicating load change, frictional force and number of revolutions in an example of measurement using a conventional apparatus and material B.

DETAILED DESCRIPTION OF THE PREFERRED EMBODIMENTS

Embodiments of the present invention will be described hereinafter with reference to the drawings.

First Embodiment

Figure 1:
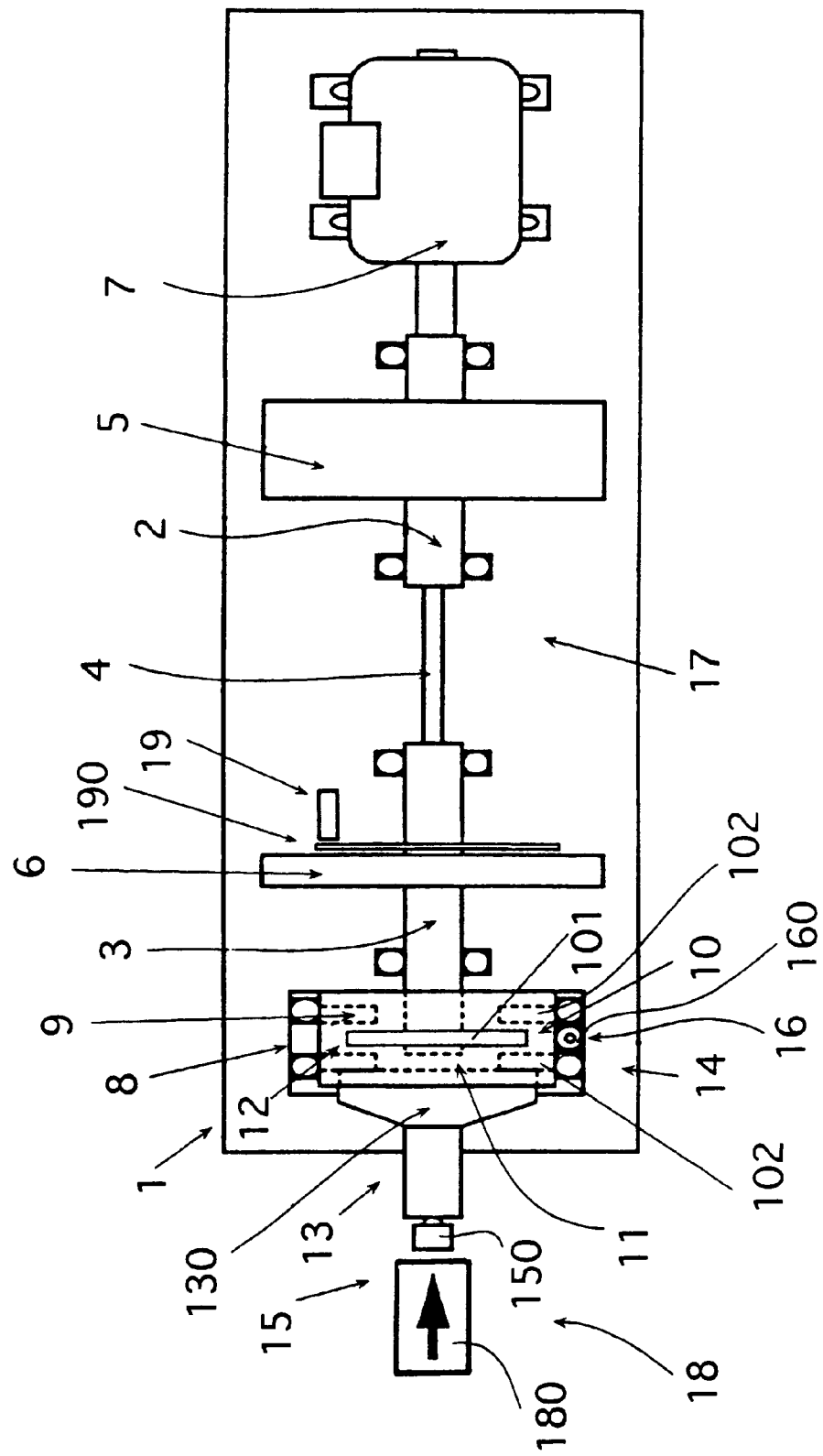
FIG. 1 is a plan view illustrating a frictional dynamic characteristic measuring apparatus according to the first embodiment of the present invention.

A frictional dynamic characteristic measuring apparatus 1 according to the first embodiment comprises, as shown in FIG. 1, a specimen holding means 11 for holding a friction material unit 10, that is, a specimen, a slide portion 12 that slidingly contacts the friction material unit 10, a pressing means 12 for pressing the slide portion 12 against the friction material unit 10, a sliding means 14 for sliding the slide portion 12 and the friction material unit 10, a pressing force detecting means 15 for detecting the pressing force, a frictional force detecting means 16 for detecting a frictional force that occurs between the slide portion 12 and the friction material unit 10, a fist sliding speed changing means 17 for changing the sliding speed of the friction material unit 10 and the sliding means 14 in a self-excited manner at a resonance frequency of a resonance system that comprises the friction material unit 10, the specimen holding means 11 and the slide portion 12, and a second sliding speed changing means 18 for forcibly changing the sliding speed of the friction material unit 10 and the slide means 14 at the resonance frequency of the resonance system.

The frictional dynamic characteristic measuring apparatus 1 includes rotating shafts 2 and 3 coaxially disposed and spaced apart from facing each other, flywheels 5 and 6 disposed on the rotating shafts 2 and 3, respectively, a torsion part 4 disposed between the facing rotating shafts 2 and 3, and a friction characteristic measuring unit 8 disposed on the rotating shaft 3.

The torsion part 4 may be formed by any member, that has a rigidity against torsion caused by a rotational difference and therefore produces a torque, such as a belt, a spring, a rubber member, or the like. In the first embodiment, the torsion part 4 is formed by a steel torsion shaft having a good linearity relative to torsion.

The rotating shaft 2 is journaled at both ends thereof. The flywheel 5 is disposed on a central portion of the rotating shaft 2. One end of the rotating shaft 2 is connected to a motor 7 which is an example of a rotational drive device, and the other end thereof is connected to the torsion shaft 4, so that rotation is transmitted from the rotating shaft 2 to the friction characteristic measuring unit 8 via the torsion shaft 4.

The rotating shaft 3 is journaled at both ends thereof. The flywheel 6 is disposed on a central portion of the rotating shaft 3. One end of the rotating shaft 6 is connected to the torsion shaft 4. A slit disc 190, that is, a device for detecting rotation of a shaft, is disposed adjacent to the flywheel 6. Disposed at the other end of the rotating shaft 3 is the friction characteristic measuring unit 8 for measuring dynamic characteristics of the friction material unit 10.

The dimensions of flywheels 5, 6 are determined by calculating the rigidity of the torsion shaft 4 and the inertia of flywheels 5, 6 so that an eigenfrequency of a torsional vibration in the vibration system of the apparatus equals a frequency desired to be measured.

The rigidity of the torsion shaft 4 is reduced by means of, for example, reducing its shaft diameter or wall thickness to a value less than that of the rotating shafts 2 and 3, in order to make the torsion shaft 4 to allow torsional vibration together with the flywheels 5, 6. Thus the torsion shaft 4 is designed so as to reliably provide a required speed change. The rotating shafts 2, 3 have a sufficient rigidity to transmit torsional vibrations caused by the torsion shaft 4 and the flywheels 5, 6.

The aforementioned elements constitute the first sliding speed changing means 17 for changing the sliding speed of the friction material unit 10 and the sliding means 14 in a self-excited manner at a resonance frequency of a resonance system comprising the friction material unit 10, the specimen holding means 11 and the slide portion 12 in the first embodiment.

Inside a case of the friction characteristic measuring unit 8, a disc-like member 101, that is, one member of the friction material unit 10 is fixed to an end of the rotating shaft 3 by a holding member so that the disc-like member 101 can rotate together with the rotating shaft 3. The other member thereof, that is, sandwich-like annular friction materials 102, is disposed and fixed in a facing arrangement inside the friction characteristic measuring unit 8.

The pressing means 13 comprises a T-shaped piston 130 against which one of the facing sandwich-like annular friction materials 102 is pressed so as to clamp the one friction material 101.

A pressing force adjusting means 180 comprises a hydraulic piston for pressurizing the piston of the pressing means 13 via a load cell 150 and a hydraulic pressure source being able to control supplied hydraulic pressure. The pressing force adjusting means 180 forcibly changes the pressing force that acts on the friction material 10. The pressing force adjusting means 180 constitutes the second sliding speed changing means 18 for forcibly changing the sliding speed of the friction material unit 10 and the sliding means 14 at the resonance frequency of the resonance system.

The pressing force detecting means 15 comprises, the load cell 150 disposed between the pressing force adjusting means 180 and the piston 130. The pressing force detecting means 15 is designed to detect the pressing force that acts on the friction material unit 10.

The frictional force detecting means 16 comprises a load cell 160 disposed on a side wall of the case for detecting a force by which the friction material 101 of the friction material unit 10 disposed inside the case of the friction characteristic measuring unit 8 rotates the annular friction materials 102 disposed in the case. The frictional force detecting means 16 is designed to detect frictional force that occurs between the slide portion 12 and the friction material unit 10 by measuring tangential force that acts on the annular friction materials 102.

A rotation sensor 19 comprises a sensor, for example, a magnetic non-contact sensor, which is disposed facing slits of the slit disc 190 disposed on the rotating shaft 3, adjacent to the flywheel 6. By counting the number of slits during rotation, number of revolutions of the rotating shaft 3 and the friction material unit 10 is detected.

The operation of the frictional dynamic characteristic measuring apparatus constructed as described above according to the first embodiment will be described below.

The motor 7 is operated in such a manner that the friction material unit 10 disposed in the case of the friction characteristic measuring unit 8 which rotates together with the rotating shaft 3, and the fly wheels 5, 6 respectively connected to the rotating shafts 2, 3 rotate at a rotational speed (number of revolutions) that provides a predetermined peripheral speed at a sliding surface of the friction material unit 10, through transmission of the rotating shaft 2, the torsion shaft 4 and the rotating shaft 3.

The friction characteristic measuring unit 8 measures a tangential force caused by a pressing force of the one friction material 101 that rotates together with the rotating shaft 3 and the other friction materials 102 disposed in the case of the friction characteristic measuring unit 8 against each other.

If the velocity gradient of the friction materials (dμ/dV value) is sufficiently negative, torsional vibrations occur at eigenfrequency of the vibration system specific to the apparatus. The frequency is determined by the torsion shaft 4, the flywheels 5, 6 and the like under certain pressing force conditions. An objective friction characteristic can easily be determined by the pressing force measured by the load cell 150, the tangential force measured by the load cell 160 and the number of revolutions measured by the sensor 19.

If the velocity gradient of the friction material unit 10 is not sufficiently negative, or if the velocity gradient of the friction material unit 10 is zero or positive, no torsional vibration will occur under certain pressing force conditions. However, torsional vibrations can be caused by changing the pressing force at an appropriate frequency using the pressing force adjusting means 180.

Although the friction coefficient thus measured contains both a load gradient by a pressing force change and a velocity gradient by a velocity change, an objective friction characteristic of the friction material can be obtained by using the following equation if the load gradient and the velocity gradient are assumed to be independent of each other.

(Tangential force)/(Load)=(0+(Load gradient) ((Load change)+ (Velocity gradient)((Velocity change)

In the above equation, (0 is a friction coefficient at a mean load and a mean velocity.

Measurement of friction characteristics "Evaluation Method 1" is performed by placing the friction material unit 10 whose friction characteristics are to be measured in the friction characteristic measuring unit 8, selecting the flywheels 5, 6 and the torsion shaft 4 so as to provide an intended velocity changing frequency, operating the motor 7 to rotate the rotating shaft 2 at a mean number of revolutions, and then applying a mean load for measurement of friction characteristics to the specimen.

If the velocity gradient of the friction coefficient of the friction material unit 10 is sufficiently negative, torsional vibration occurs in this step so that an objective friction characteristic can be measured. If no torsional vibration occurs, a load change approximate to a torsion resonance frequency that is characteristic of the apparatus is applied to the mean load by the pressing force adjusting means 180, so that a change occurs in the torsional torque. Thereby, a rotation change by vibration can be caused, in addition to the constant speed rotation produced by the motor 7.

This rotation change is measured by a means for detecting positions of slits of the disc 190 disposed to rotate together with the rotating shaft 3 connected to the friction materials, and thereby determining rotation. By detecting constant signals relative to rotational angle and measuring intervals between the signals, instantaneous rotation of the friction characteristic measuring unit 8 between the signals can be determined.

It becomes possible to detect more minute and accurate rotation change if the number of signals generated during one rotation is increased by increasing the number of slits formed in the disc 190. A friction coefficient corresponding to the thus-measured instantaneous number of revolutions, that is, an instantaneous velocity, is calculated. Using the thus-calculated instantaneous friction coefficient, load change and velocity change, a velocity gradient and a load gradient can be calculated.

Figure 2:
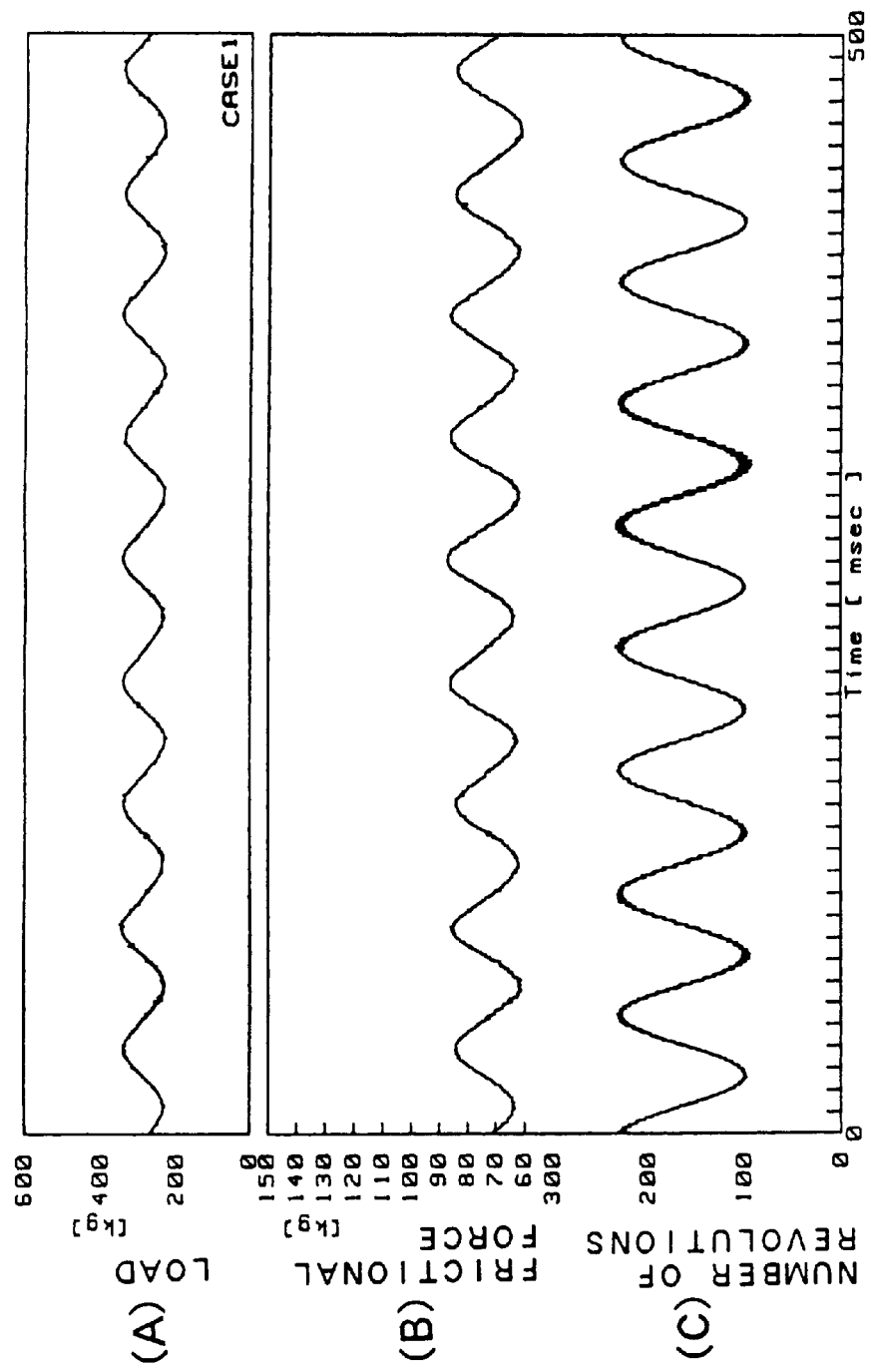
FIG. 2 shows graphs indicating load change, frictional force and number of revolutions in an example of measurement using the apparatus of the first embodiment.

FIG. 2 is based on an example wherein characteristics of friction materials B were specified using the apparatus according to the first embodiment. As for the measurement conditions, friction was caused in a lubricating oil, and the oil temperature was 80 C., and the load was a changing load. FIG. 2 indicates, from above, changes in load, frictional force (tangential force) and number of revolutions over time. The time through the abscissa axis is 0.5 second. The load is a changing load wherein the mean load was about 300 kg, and a changing load at a frequency of about 18 Hz with an amplitude of about 50 kg was applied. The resultant number of revolutions was a changing number of revolutions wherein the mean number of revolutions was about 150 rpm, the amplitude was about 60 rpm, and the frequency was about 18 Hz. The tangential force also changed at about 18 Hz.

From results of the measurement, a velocity gradient of friction coefficient is calculated as about –0.001 (sec/m). From measurements of another friction material A with poor characteristics, the velocity gradient of friction coefficient is about –0.01 (sec/m). Thus, it is clear that the ability of the friction material B to undergo friction vibration is sufficiently lower than that of the friction material A with poor characteristics.

Such differences between the friction materials may become clear or may not become clear depending on machines in which the friction materials are used. Evaluation will differ depending on attenuation of vibration of machines for use. If the machine sufficiently attenuates vibration, neither of the friction materials will not undergo vibration. Depending on the attenuation value, only the poor material will vibrate.

In the frictional dynamic characteristic measuring apparatus according to the first embodiment, the pressing force detecting means 15 detects a pressing force and the frictional force detecting means 16 detects a frictional force that occurs between the slide portion and the friction material in a state where the first sliding speed changing means 17 changes a sliding speed of the friction material and the sliding means in a self-excited manner at a resonance frequency of a resonance system comprising the friction material, the specimen holding means and the slide portion, and where the second sliding speed changing means 18 forcibly changes the sliding speed of the friction material and the sliding means at the resonance frequency of the resonance system. Therefore, the apparatus of the first embodiment achieves advantages of enabling evaluation of possibility of occurrence of vibration in a friction material that absorbs self-excited vibration in a torsional vibration system as well as enabling evaluation of the tendency of the friction material unit 20 to vibrate.

Further, since the frictional dynamic characteristic measuring apparatus of the first embodiment measures a velocity gradient of friction characteristics of the friction material unit 10 while changing the velocity at a frequency that becomes critical in an actual use, the apparatus achieves advantages of further improving from the conventional level the precision in evaluation regarding friction vibration that will occur in actual use of the material. Thus, the apparatus no longer requires the evaluation in an actual machine that is indispensable in the conventional evaluation, and realizes efficient development of materials.

Further, since the frictional dynamic characteristic measuring apparatus of the first embodiment enables evaluation in a test apparatus, the measuring apparatus of the embodiment receives reduced external disturbances and therefore facilitates environment setting and provides improved precision and reproducibility, compared with evaluation in an actual machine in which friction materials will be actually used. Therefore, the apparatus of the embodiment achieves an advantages of enabling efficient development and improvement of friction materials.

Further, since the frictional dynamic characteristic measuring apparatus of the first embodiment enables evaluation regarding friction vibration on a higher level, than that in the prior art, the apparatus achieves advantages of realizing a margin in design with respect to unexpected external disturbances and degradations of friction characteristics and of further improving reliabilities in products.

Further, the frictional dynamic characteristic measuring apparatus of the first embodiment applies oscillation at a frequency in accordance with an objective oscillation frequency in an apparatus for measuring frictional dynamic characteristics and, thereby, provides a predetermined velocity change in the velocity of the friction characteristic measuring unit 8. Therefore, the apparatus of the first embodiment achieves an advantage of enabling more practical measurement of friction characteristics.

Moreover, if it is intended that frictional vibrations of an actual machine be controlled by a friction material used, the frictional dynamic characteristic measuring apparatus of the first embodiment achieves an advantage of providing a method for evaluating a friction material alone in accordance with actual phenomena whereby the control is facilitated.

Further, since the frictional dynamic characteristic measuring apparatus of the first embodiment simplifies the test wherein not only the evaluation of a friction material alone but also evaluation in an actual machine were performed, the apparatus of the embodiment achieves an advantage of contributing to establishment of an efficient technique for controlling frictional vibrations.

Moreover, the frictional dynamic characteristic measuring apparatus of the first embodiment can be applied to a wide variety of evaluation regarding frictional vibration control. That is, the apparatus can be applied to not only evaluation of materials with low capability to suppress frictional vibration, that is, materials that readily undergo frictional vibration, but also evaluation of friction materials within ranges where no frictional vibration will occur when the material is used in an actual machine as evaluation of capability to suppress friction vibrations. Therefore, the apparatus of the embodiment achieves an advantage of contributing to development of better friction materials, for example, improving the capability to suppress frictional vibrations in accordance with changes in use conditions if the friction material is used in an actual machine.

Further, the frictional dynamic characteristic measuring apparatus of the first embodiment achieves an advantage of making it possible to measure a velocity gradient ($d\mu/dV$) of the friction coefficient $\mu$ that may cause frictional vibration, under conditions where the velocity changes at a frequency of frictional vibration.

Moreover, in the frictional dynamic characteristic measuring apparatus of the first embodiment, since the vibration system is disposed in such a manner that the friction velocity is changed, it advantageously becomes possible to measure friction under conditions where the velocity changes at a predetermined frequency. Further, since friction characteristics are measured by performing operation to provide a predetermined velocity change in friction coefficient, it advantageously becomes possible to evaluate a friction material alone regarding frictional vibration.

Second Embodiment

Figure 3:
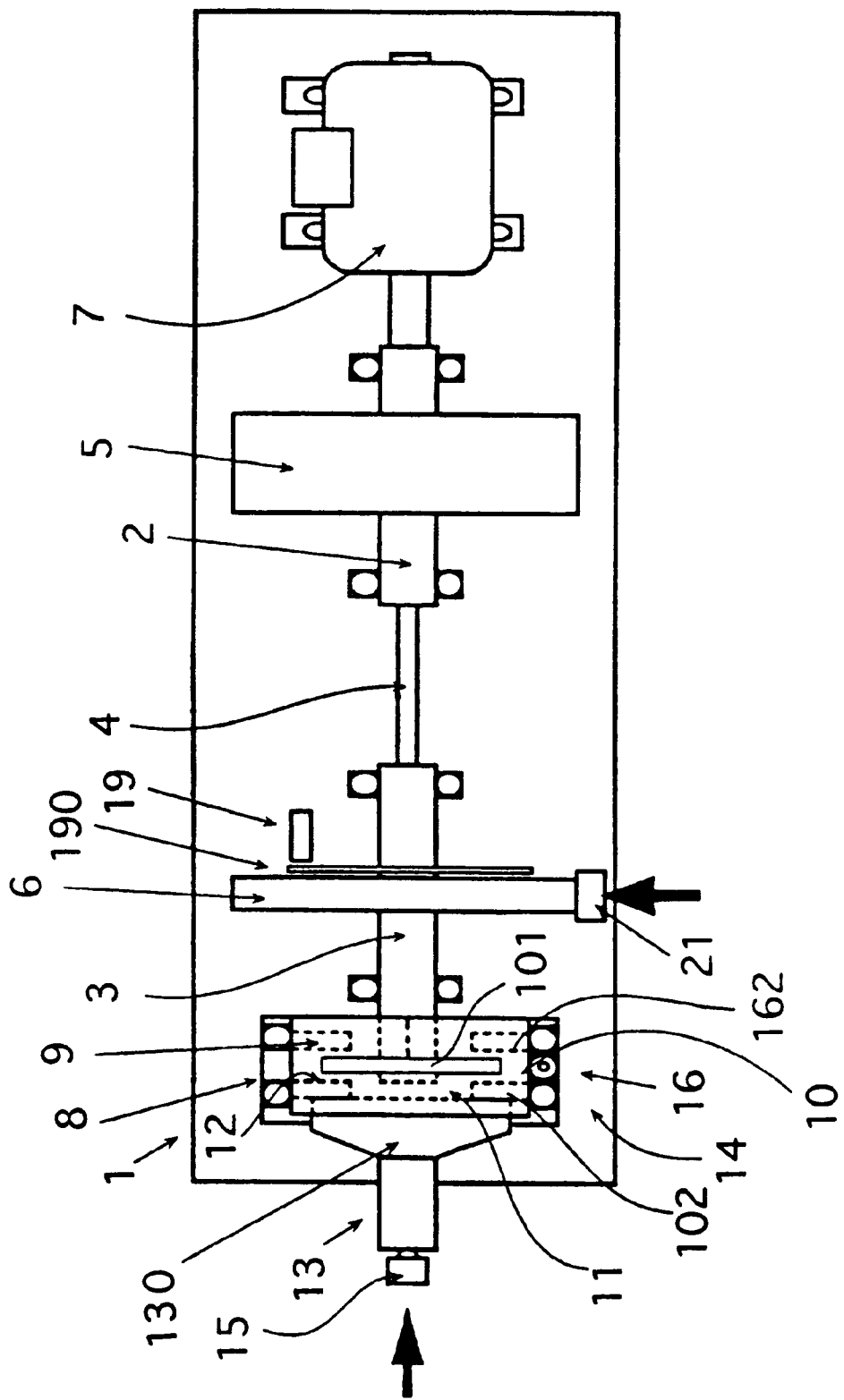
FIG. 3 is a plan view illustrating a frictional dynamic characteristic measuring apparatus according to the second embodiment of the present invention.

A frictional dynamic characteristic measuring apparatus 1 according to a second embodiment is based on the first embodiment and designed to measure only velocity gradient of friction coefficient of a friction member, as indicated in FIG. 3.

The frictional dynamic characteristic measuring apparatus of the second embodiment is distinguished in the following respect. In the first embodiment, after a mean load is applied to a friction material by the piston 130, the load was changed in order to give a torsional torque to the flywheel 6 and, thereby, achieve torsional vibration. However, the second embodiment provides a torsional torque change by changing the braking force on the flywheel 6.

In the friction characteristic measuring unit 8, there is no need to consider load gradient in measured data since there is no load change. Data arrangement is thereby made easy. The following equation is used:

$$(\text{Tangential force})/(\text{Load}) = \mu_0 + (\text{Velocity gradient}) \times (\text{Velocity change})$$

In the above equation, $\mu_0$ is a friction coefficient at a mean load and a mean velocity, and the velocity change is a change from the mean velocity.

In the second embodiment, a braking force changing means 21 comprises a friction material, and a piston able to change pressing force on the friction material. By changing the braking force that acts on the flywheel 6, the braking force changing means 21 changes torsional torque to achieve torsional vibration.

Since the frictional dynamic characteristic measuring apparatus of the second embodiment eliminates the need to consider load gradient in data processing unlike the first embodiment, the second embodiment is more suitable for measurement of a material that has a load gradient of friction coefficient which affects the velocity gradient.

While the frictional dynamic characteristic measuring apparatus of the first embodiment is unable to increase the load change in order to achieve torsional vibration if the mean load is small, the frictional dynamic characteristic measuring apparatus of the second embodiment is able to control it independently. Therefore, the apparatus of the second embodiment is advantageously able to cause torsional vibration regardless of the magnitude of mean load.

An example of measurement of characteristics of a friction material using the apparatus of the second embodiment will be described below. As for measurement conditions, the load was about 300 kg, and the number of revolutions was a changing number of revolutions wherein the mean number of revolutions was about 150 rpm, and the amplitude was about 100 rpm, and the frequency was about 18 Hz. Other conditions were the same as in the example of measurement using the first embodiment, that is, friction was caused in a lubricating oil, and the oil temperature was 80° C.

Figure 4:
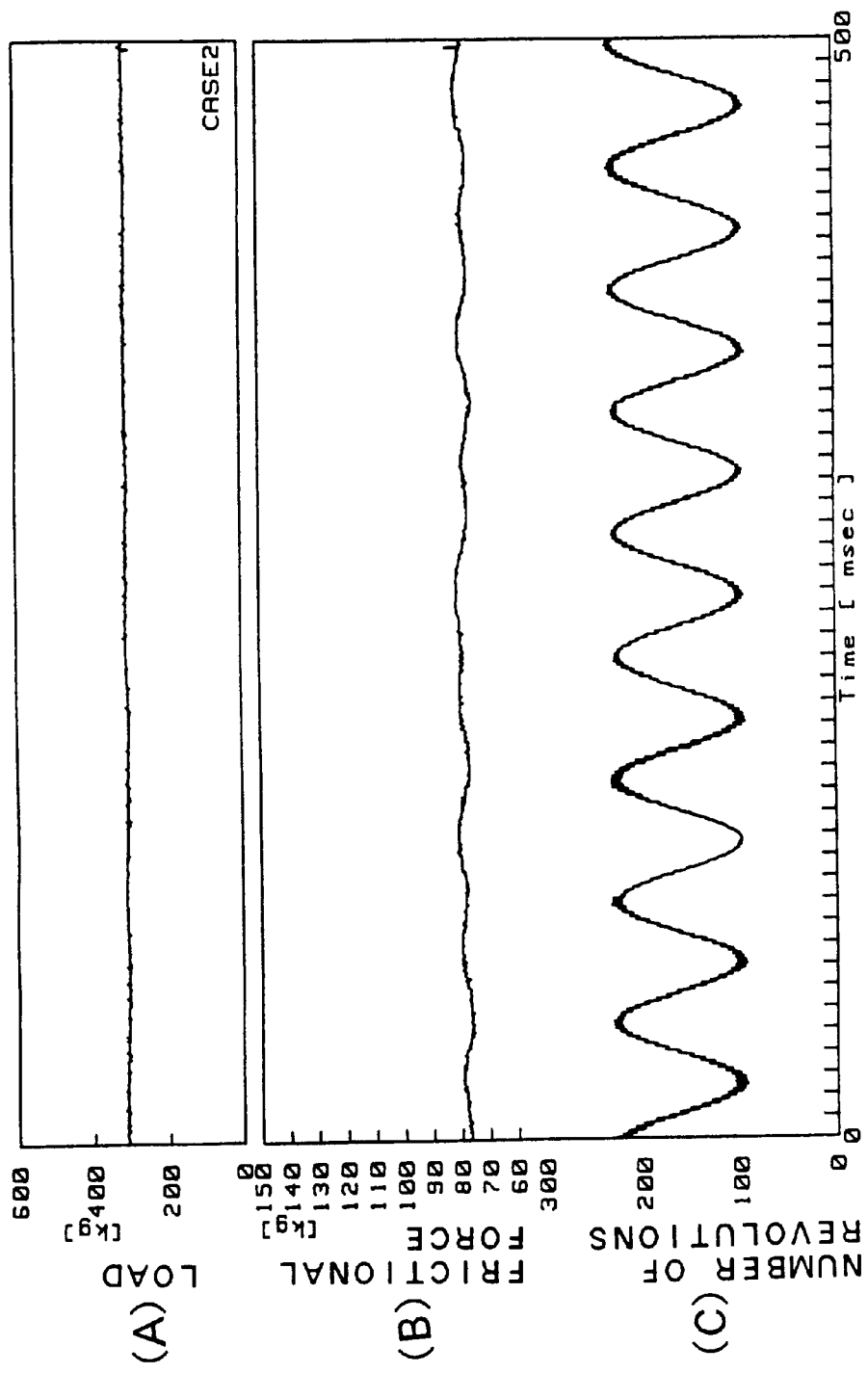
FIG. 4 shows graphs indicating load change, frictional force and number of revolutions in an example of measurement using the apparatus of the second embodiment.
Figure 5:
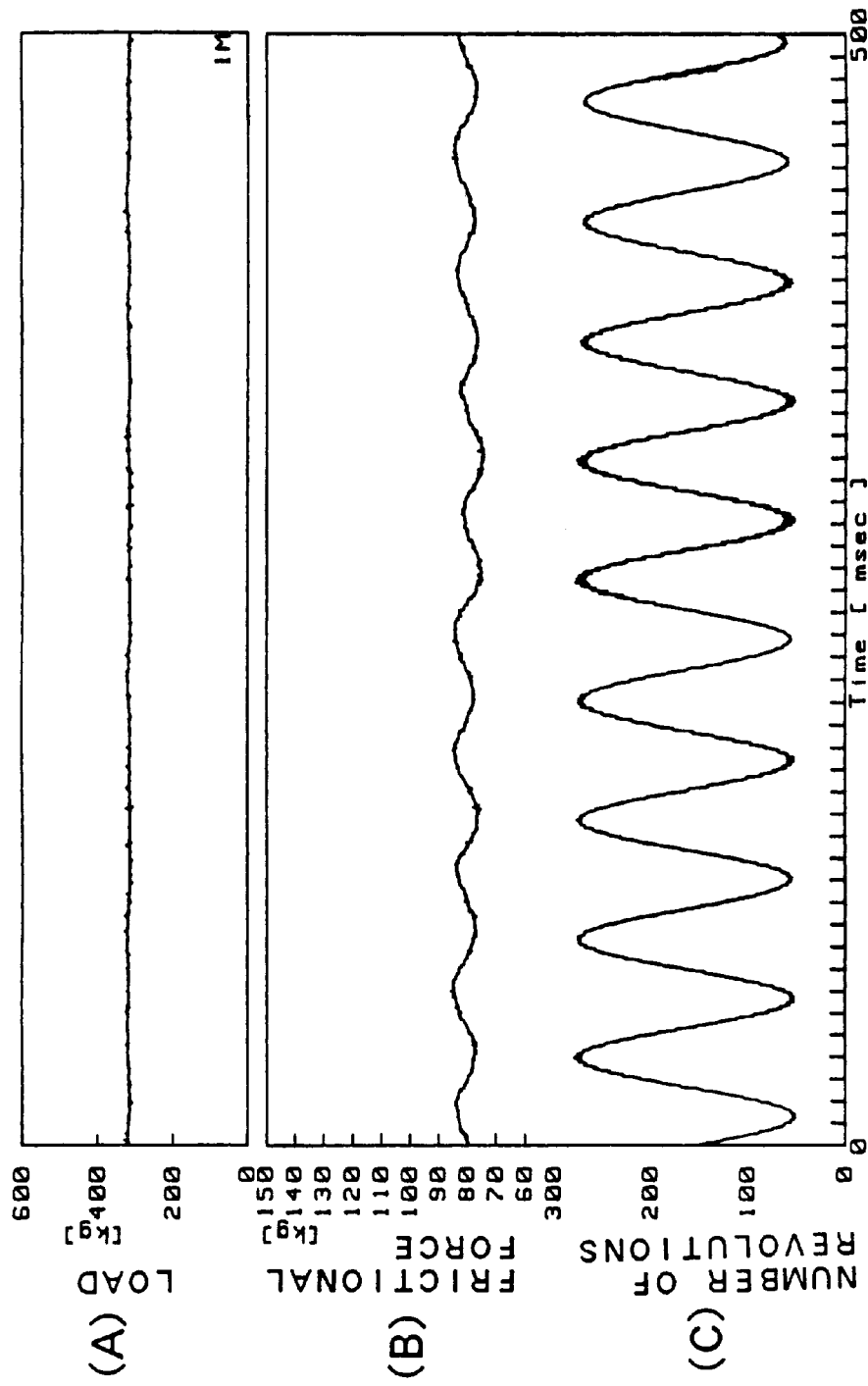
FIG. 5 shows graphs indicating load change, frictional force and number of revolutions in an example of measurement using a conventional apparatus and material A.

FIG. 4 indicates results similar to those in FIG. 2. The velocity gradient of fiction coefficient calculated from measurement results is the same as the value calculated from measurement results indicated in FIG. 2. The calculation is easier in the case indicated in FIG. 4 than case indicated in FIG. 2. Further, since the tangential force did not change despite load changes, there is no influence thereby and, therefore, it is possible to determine a pure velocity gradient of friction coefficient.

The preferred embodiments of the present invention, as herein disclosed, are taken as some embodiments for explaining the present invention. It is to be understood that the present invention should not be restricted by these embodiments and any modifications and additions are possible so far as they are not beyond the technical idea or principle based on descriptions of the scope of the patent claims.

What is claimed is:

1. A frictional dynamic characteristic measuring apparatus for measuring a pressing force and a frictional force acting between a friction material and a slide portion which are in sliding contact, comprising:
    a drive means for rotating said friction material at a predetermined peripheral speed with respect to said slide portion; and
    a sliding speed changing member for forcibly changing, at a resonance frequency of a resonance system, the predetermined sliding speed of said friction material and said slide portion, which changes in a self-excited manner at the resonance frequency of the resonance system, said resonance system including said friction material and said slide portion.

2. A friction dynamic characteristic measuring apparatus comprising:
    holding means for holding a friction material as a specimen;
    a slide portion slidingly contacting said friction material;
    pressing means for pressing said slide portion to said friction material;
    sliding means for sliding said slide portion and said friction material;
    pressing force detecting means for detecting a pressing force of said pressing means;
    frictional force detecting means for detecting a frictional force that occurs between said slide portion and said friction material;
    first sliding speed changing means for self-excitedly changing a sliding speed of said friction material and said sliding means at a resonance frequency of a resonance system comprising said friction material, said holding means and said slide portion; and
    second sliding speed changing means for forcibly changing the sliding speed of said friction material and said sliding means at said resonance frequency of said resonance system.

3. A frictional dynamic characteristic measuring apparatus according to claim 2, wherein
    said second sliding speed changing means comprises external force changing means for changing an external force acting on said resonance system.

4. A frictional dynamic characteristic measuring apparatus according to claim 3, wherein
    said external force changing means comprises pressing force changing means for changing a pressing force.

5. A frictional dynamic characteristic measuring apparatus according to claim 3, wherein
    said external force changing means comprises braking force applying means for applying a braking force to a rotating body in said resonance system.

6. A frictional dynamic characteristic measuring apparatus according to claim 5, wherein said first sliding speed changing means comprises
    rotating shafts coaxially disposed and spaced apart from each other in opposing arrangement,
    flywheels respectively disposed on said rotating shafts,
    a torsion part disposed between said opposed rotating shafts, and
    a friction characteristic measuring unit disposed on one of said rotating shafts.

7. A frictional dynamic characteristic measuring apparatus according to claim 6, wherein
    said torsion part is formed by a member, for producing a torque and having a predetermined rigidity against torsion caused by a rotational difference, selected from the group consisting of a belt, a spring, a rubber member, and a steel torsion shaft having a good linearity relative to torsion.

8. A frictional dynamic characteristic measuring apparatus according to claim 7, wherein
    one of said rotating shafts having one of said flywheels disposed on a central portion thereof is journaled at both ends thereof and is connected to a motor at one end thereof and to said torsion part at the other end thereof.

9. A frictional dynamic characteristic measuring apparatus according to claim 8, wherein
    another of said rotating shafts having another of said flywheels disposed on a central portion thereof is journaled at both ends thereof,
    a slit disc as a device for detecting rotation thereof is disposed adjacent to said flywheel,
    said torsion part is connected to one end of said another of the rotating shafts and
    said friction characteristic measuring unit is connected to the other end thereof.

10. A frictional dynamic characteristic measuring apparatus according to claim 9, wherein
    dimensions of said flywheels are determined by calculating the inertia thereof the rigidity of said torsion shaft so that eigenfrequency of a torsional vibration in said vibration system equals a desired frequency.

11. A frictional dynamic characteristic measuring apparatus according to claim 10, wherein
    said torsion part comprises a steel torsion shaft having a smaller diameter than that of said rotating shafts, in order to allow torsional vibration and to obtain a good linearing with respect to torsion.

12. A frictional dynamic characteristic measuring apparatus according to claim 11, wherein
    said friction material comprises a disc-like friction material and two annular friction materials, and
    said friction characteristic measuring unit comprises a case, in which said two annular friction materials are opposedly disposed, and said disc-like friction material fixed to one end of said another of the rotating shafts is interposed between said annular friction materials.

13. A frictional dynamic characteristic measuring apparatus according to claim 12, wherein
    said pressing means comprises a T-shaped piston for pressing one of said annular friction materials so as to clamp said disc-like friction material.

14. A frictional dynamic characteristic measuring apparatus according to claim 13, wherein
    said friction force detecting means comprises a load cell disposed on a side wall of said case, for detecting a friction force occurring between said slide portion and said friction material unit by measuring tangential force acting on said annular friction materials.

15. A frictional dynamic characteristic measuring apparatus according to claim 14, further comprising a rotation sensor, disposed on facing slits of said slit disc, for counting the number of said slits during rotation and detecting a number of revolutions of said rotating shaft and said friction material unit.

16. A frictional dynamic characteristic measuring apparatus according to claim 15, wherein said second sliding speed changing means comprises pressing force adjusting means including a hydraulic piston for pressing said T-shaped piston and a hydraulic pressure source for controlling supplied hydraulic pressure in order to forcibly control the pressing force acting on said friction material and to control the sliding speed of said friction material unit and said sliding means at said resonance frequency of said resonance system.

17. A frictional dynamic characteristic measuring apparatus according to claim 16, wherein said pressing force detecting means comprises a load cell disposed between said pressing force adjusting means and said hydraulic piston, in order to detect the pressing force acting on said friction material.

18. A frictional dynamic characteristic measuring apparatus according to claim 15, wherein said second sliding speed changing means comprises pressing force adjusting means comprising a braking force controlling means in order to control a brake force applied to an outer peripheral wall of said another of the flywheels disposed on another of said rotating shafts.

19. A frictional dynamic characteristic measuring apparatus according to claim 1, wherein said sliding speed changing member comprises a means for self-excitedly changing a sliding speed of said friction material and said slide portion at a resonance frequency of a torsional vibration system.

20. A frictional dynamic characteristic measuring apparatus according to claim 1, wherein said drive means comprises a motor for producing the predetermined peripheral speed of said friction material.

\* \* \* \* \*